United States Patent
Jakel et al.

(10) Patent No.: US 10,480,038 B2
(45) Date of Patent: Nov. 19, 2019

(54) SYSTEM AND METHOD FOR PRODUCING A SUGAR STREAM

(71) Applicant: Fluid Quip Process Technologies, LLC, Springfield, OH (US)

(72) Inventors: Neal Jakel, Cedar Rapids, IA (US); Albert Pollmeier, Cedar Rapids, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 15/957,242

(22) Filed: Apr. 19, 2018

(65) Prior Publication Data

US 2019/0323097 A1    Oct. 24, 2019

(51) Int. Cl.
| | |
|---|---|
| C13K 1/08 | (2006.01) |
| C12M 1/00 | (2006.01) |
| C12P 7/06 | (2006.01) |
| C12P 7/16 | (2006.01) |

(52) U.S. Cl.
CPC .............. C13K 1/08 (2013.01); C12M 43/00 (2013.01); C12P 7/06 (2013.01); C12P 7/16 (2013.01)

(58) Field of Classification Search
None
See application file for complete search history.

(56) References Cited

U.S. PATENT DOCUMENTS

| | | | |
|---|---|---|---|
| 4,330,625 A | 5/1982 | Miller et al. | |
| 4,361,651 A | 11/1982 | Keim | |
| 4,407,955 A | 10/1983 | Muller et al. | |
| 4,578,353 A | 3/1986 | Assarsson et al. | |
| 6,962,722 B2 | 11/2005 | Dawley et al. | |
| 7,452,425 B1 | 11/2008 | Langhauser | |
| 7,488,390 B2 | 2/2009 | Langhauser | |
| 7,494,675 B2 | 2/2009 | Abbas et al. | |
| 7,985,847 B2 | 7/2011 | Belanger et al. | |
| 8,278,080 B2 | 10/2012 | Yoon | |
| 8,557,540 B2 | 10/2013 | Burlew et al. | |
| 8,652,818 B2 | 2/2014 | Lawton, Jr. et al. | |
| 8,722,372 B2 | 5/2014 | Kiuchi et al. | |
| 8,778,433 B2 | 7/2014 | Lee | |
| 9,012,191 B2 | 4/2015 | Lee | |
| 9,068,205 B2 | 6/2015 | Purtle et al. | |
| 9,273,329 B2 | 3/2016 | Kusuda et al. | |
| 9,523,104 B2 | 12/2016 | Fuchs et al. | |
| 9,909,158 B2 | 3/2018 | Yamada et al. | |
| 9,920,346 B2 | 3/2018 | Funada et al. | |
| 9,926,613 B2 | 3/2018 | Kishimoto et al. | |
| 2006/0083823 A1 | 4/2006 | Fox et al. | |
| 2006/0251762 A1 | 11/2006 | Jansen et al. | |
| 2007/0014905 A1 | 1/2007 | Chen et al. | |
| 2007/0020375 A1 | 1/2007 | Jansen et al. | |
| 2008/0260902 A1 | 10/2008 | Van Houten et al. | |
| 2009/0238918 A1 | 9/2009 | Jansen et al. | |
| 2009/0258106 A1 | 10/2009 | Jansen et al. | |
| 2011/0236946 A1 | 9/2011 | Maclachlan et al. | |
| 2012/0244590 A1 | 9/2012 | Lee | |
| 2013/0065289 A1 | 3/2013 | Carlson | |
| 2013/0236936 A1 | 9/2013 | Lee | |
| 2013/0295661 A1 | 11/2013 | Roesch et al. | |
| 2014/0024064 A1 | 1/2014 | Burlew et al. | |
| 2014/0193872 A1 | 7/2014 | Chen et al. | |
| 2014/0227757 A1 | 8/2014 | Jin et al. | |
| 2014/0234935 A1 | 8/2014 | Kusuda et al. | |
| 2014/0287469 A1 | 9/2014 | Medoff et al. | |
| 2014/0356915 A1 | 12/2014 | Retsina et al. | |
| 2015/0004647 A1 | 1/2015 | Niwa et al. | |
| 2015/0344921 A1 | 12/2015 | Kacmar et al. | |
| 2016/0160242 A1 | 6/2016 | Mimitsuka et al. | |
| 2016/0186215 A1 | 6/2016 | Redford | |
| 2016/0289704 A1 | 10/2016 | Medoff | |
| 2016/0289705 A1 | 10/2016 | Medoff | |
| 2016/0289706 A1 | 10/2016 | Medoff | |
| 2016/0298141 A1 | 10/2016 | Medoff | |
| 2016/0298142 A1 | 10/2016 | Yu et al. | |
| 2016/0312258 A1 | 10/2016 | Ikeo et al. | |
| 2017/0022466 A1* | 1/2017 | Jakel | ........................ C12P 19/02 |

FOREIGN PATENT DOCUMENTS

| | | | | |
|---|---|---|---|---|
| EP | 3121258 A1 | 1/2017 | | |
| WO | WO-2012129500 A2 * | 9/2012 | ............ | C12M 21/12 |
| WO | 2014182807 A1 | 11/2014 | | |

OTHER PUBLICATIONS

European Patent Office, Extended Search Report issued in EP 19 166 443.2 dated Jul. 26, 2019, 9 pages.

* cited by examiner

*Primary Examiner* — Robert J Yamasaki
(74) *Attorney, Agent, or Firm* — Wood Herron & Evans LLP

(57) ABSTRACT

An improved dry grind system and method for producing a sugar stream from grains or similar carbohydrate sources and/or residues, such as for biochemical production. In particular, after saccharification and prior to a sugar conversion process, a sugar/carbohydrate stream is removed from a saccharified stream. The sugar/carbohydrate stream includes a desired Dextrose Equivalent (DE) where DE describes the degree of conversion of starch to dextrose can be produced, with the such sugar stream being available for biochemical production, e.g., alcohol production, or other processes. In addition, the systems and methods also can involve the removal of certain grain components, e.g., corn kernel components, including protein and/or fiber. Sugar stream production occurs on the front end of the system and method.

27 Claims, 4 Drawing Sheets

SYSTEM AND METHOD FOR PRODUCING A SUGAR STREAM

TECHNICAL FIELD

The present invention relates generally to systems and methods for use in the biochemical (e.g., biofuel), food, feed, nutrition, enzymes, amino acids, proteins, and/or pharmacy industries and, more specifically, to improved dry grind systems and methods for producing a sugar stream, such as for biochemical production.

BACKGROUND

The conventional processes for producing various types of biochemicals, such as biofuels (e.g., alcohol) and other chemicals, from grains generally follow similar procedures. Wet mill processing plants convert, for example, corn grain, into several different co-products, such as germ (for oil extraction), gluten feed (high fiber animal feed), gluten meal (high protein animal feed) and starch-based products such as alcohol (e.g., ethanol or butanol), high fructose corn syrup, or food and industrial starch. Dry grind plants generally convert grains, such as corn, into two products, namely alcohol (e.g., ethanol or butanol) and distiller's grains with solubles. If sold as wet animal feed, distiller's wet grains with solubles are referred to as DWGS. If dried for animal feed, distiller's dried grains with solubles are referred to as DDGS. This co-product provides a secondary revenue stream that offsets a portion of the overall alcohol production cost.

Figure 1:
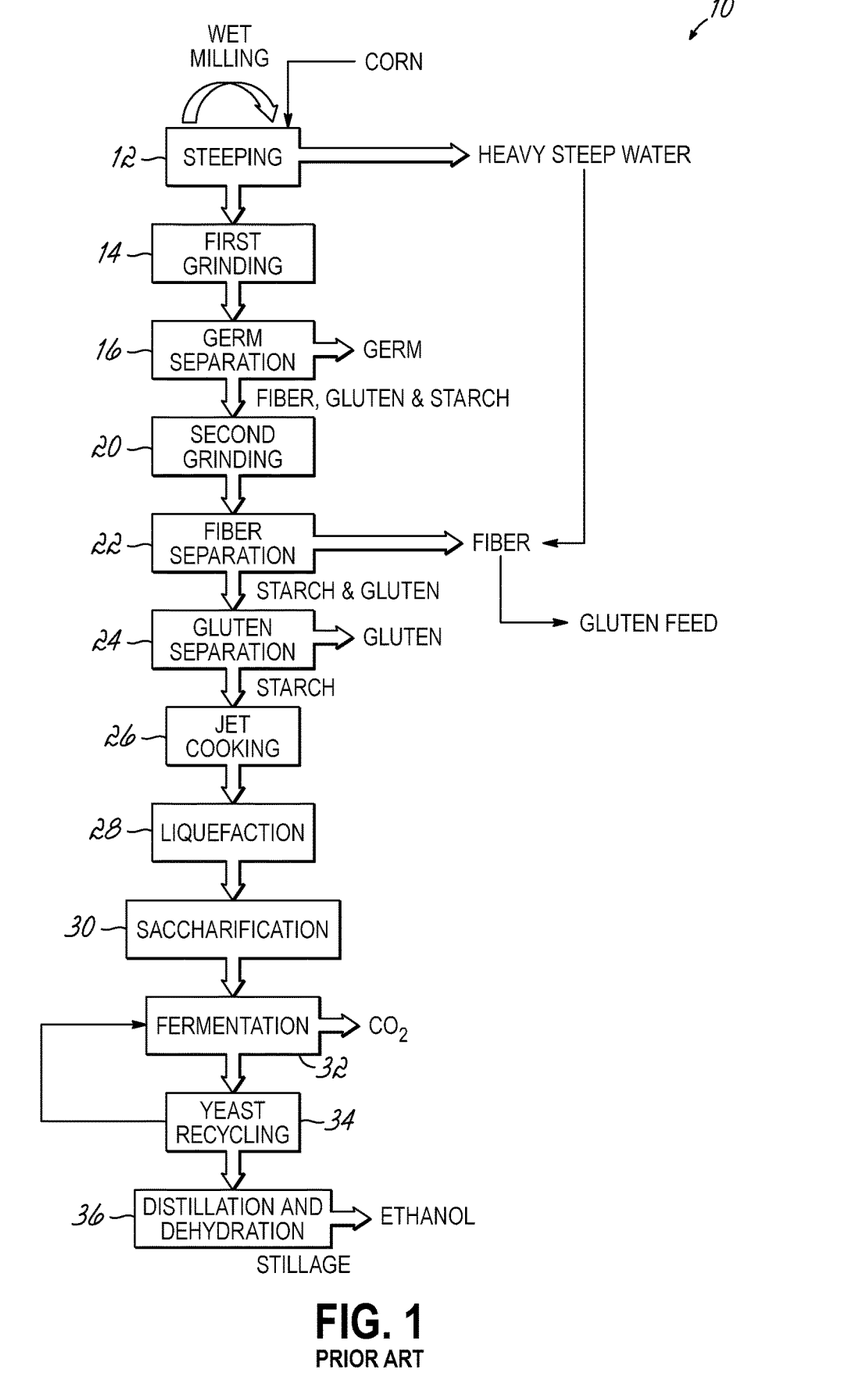
FIG. 1 is a flow diagram of a typical wet mill alcohol production process.

With respect to the wet mill process, FIG. 1 is a flow diagram of a typical wet mill alcohol (e.g., ethanol) production process 10. The process 10 begins with a steeping step 12 in which grain (e.g., corn) is soaked for 24 to 48 hours in a solution of water and sulfur dioxide in order to soften the kernels for grinding, leach soluble components into the steep water, and loosen the protein matrix with the endosperm. Corn kernels contain mainly starch, fiber, protein, and oil. The mixture of steeped corn and water is then fed to a degermination mill step (first grinding) 14 in which the corn is ground in a manner that tears open the kernels and releases the germ so as to make a heavy density (8.5 to 9.5 Be) slurry of the ground components, primarily a starch slurry. This is followed by a germ separation step 16 that occurs by flotation and use of a hydrocyclone(s) to separate the germ from the rest of the slurry. The germ is the part of the kernel that contains the oil found in corn. The separated germ stream, which contains some portion of the starch, protein, and fiber, goes to germ washing to remove starch and protein, and then to a dryer to produce about 2.7 to 3.2 pounds (dry basis) of germ per bushel of corn (lb/bu). The dry germ has about 50% oil content on a dry basis.

The remaining slurry, which is now devoid of germ but contains fiber, gluten (i.e., protein), and starch, is then subjected to a fine grinding step (second grinding) 20 in which there is total disruption of endosperm and release of endosperm components, namely gluten and starch, from the fiber. This is followed by a fiber separation step 22 in which the slurry is passed through a series of screens in order to separate the fiber from starch and gluten and to wash the fiber clean of gluten and starch. The fiber separation stage 22 typically employs static pressure screens or rotating paddles mounted in a cylindrical screen (i.e., paddle screens). Even after washing, the fiber from a typical wet grind mill contains 15 to 20% starch. This starch is sold with the fiber as animal feed. The remaining slurry, which is now generally devoid of fiber, is subjected to a gluten separation step 24 in which centrifugation or hydrocyclones separate starch from the gluten. The gluten stream goes to a vacuum filter and dryer to produce gluten (protein) meal.

The resulting purified starch co-product then can undergo a jet cooking step 26 to start the process of converting the starch to sugar. Jet cooking refers to a cooking process performed at elevated temperatures and pressures, although the specific temperatures and pressures can vary widely. Typically, jet cooking occurs at a temperature of about 93 to 110° C. (about 200 to 230° F.) and a pressure of about 30 to 50 psi. This is followed by liquefaction 28, saccharification 30, fermentation 32, yeast recycling 34, and distillation/dehydration 36 for a typical wet mill biochemical system. Liquefaction occurs as the mixture or "mash" is held at 80 to 95° C. in order for alpha-amylase to hydrolyze the gelatinized starch into maltodextrins and oligosaccharides (chains of glucose sugar molecules) to produce a saccharafied mash or slurry. In the saccharification step 30, the liquefied mash is cooled to about 50° C. and a commercial enzyme known as gluco-amylase is added. The gluco-amylase hydrolyzes the maltodextrins and short-chained oligosaccharides into single glucose sugar molecules to produce a liquefied mash. In the fermentation step 32, a common strain of yeast (*Saccharomyces cerevisae*) is added to metabolize the glucose sugars into ethanol and $CO_2$.

Upon completion, the fermentation mash ("beer") will contain about 15% to 18% ethanol (volume/volume basis), plus soluble and insoluble solids from all the remaining grain components. The solids and some liquid remaining after fermentation go to an evaporation stage where yeast can be recovered as a byproduct. Yeast can optionally be recycled in a yeast recycling step 34. In some instances, the $CO_2$ is recovered and sold as a commodity product. Subsequent to the fermentation step 32 is the distillation and dehydration step 36 in which the beer is pumped into distillation columns where it is boiled to vaporize the ethanol. The ethanol vapor is separated from the water/slurry solution in the distillation columns and alcohol vapor (in this instance, ethanol) exits the top of the distillation columns at about 95% purity (190 proof). The 190 proof ethanol then goes through a molecular sieve dehydration column, which removes the remaining residual water from the ethanol, to yield a final product of essentially 100% ethanol (199.5 proof). This anhydrous ethanol is now ready to be used for motor fuel purposes. Further processing within the distillation system can yield food grade or industrial grade alcohol.

No centrifugation step is necessary at the end of the wet mill ethanol production process 10 as the germ, fiber, and gluten have already been removed in the previous separation steps 16, 22, 24. The "stillage" produced after distillation and dehydration 36 in the wet mill process 10 is often referred to as "whole stillage" although it also is technically not the same type of whole stillage produced with a traditional dry grind process described in FIG. 2 below, since no insoluble solids are present. Other wet mill producers may refer to this type of stillage as "thin" stillage.

The wet grind process 10 can produce a high quality starch product for conversion to alcohol, as well as separate streams of germ, fiber, and protein, which can be sold as co-products to generate additional revenue streams. However, the overall yields for various co-products can be less than desirable and the wet grind process is complicated and costly, requiring high capital investment as well as high-energy costs for operation.

Figure 2:
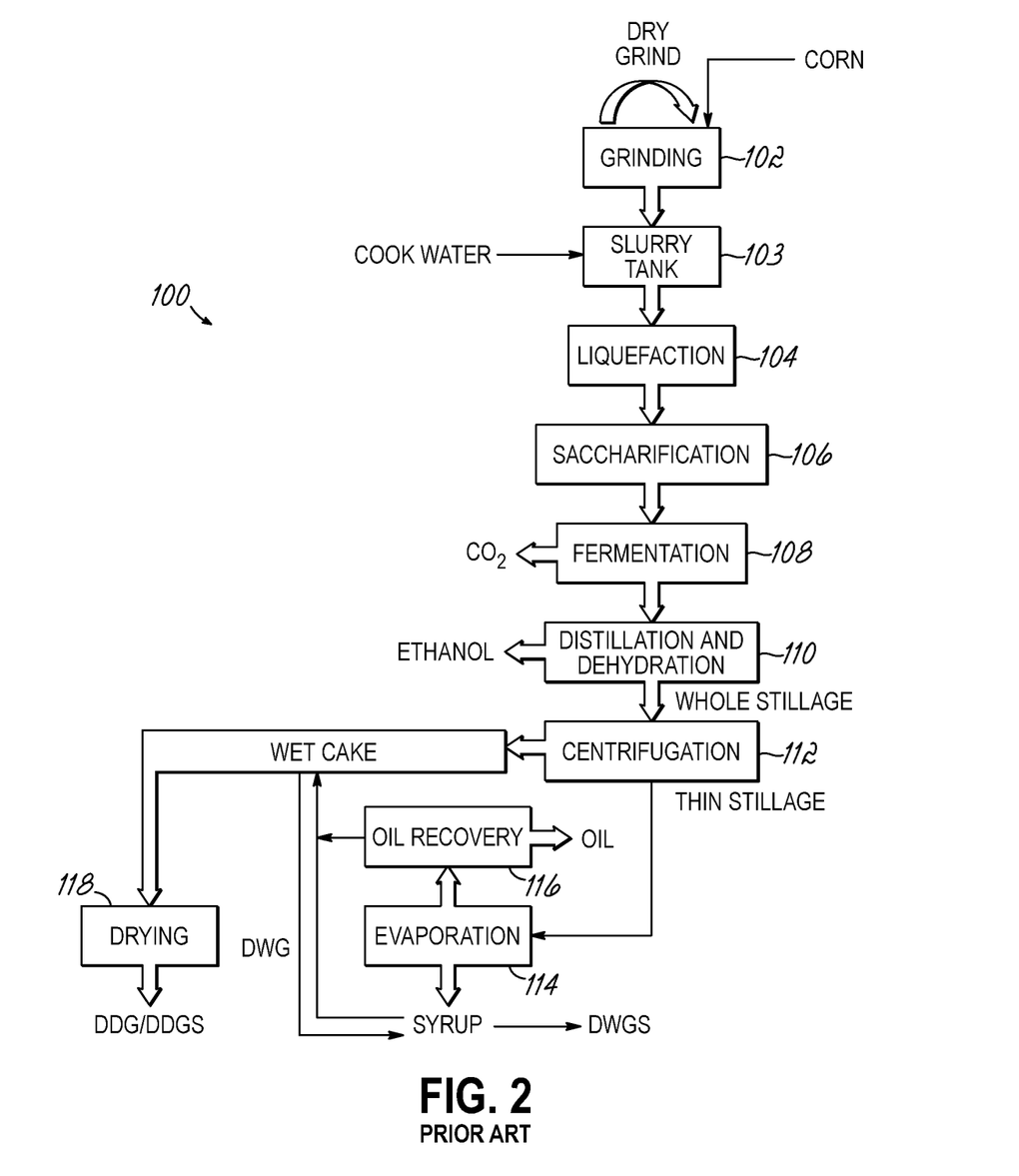
FIG. 2 is a flow diagram of a typical dry grind alcohol production process.

Because the capital cost of wet grind mills can be so prohibitive, some alcohol plants prefer to use a simpler dry grind process. FIG. 2 is a flow diagram of a typical dry grind alcohol (e.g., ethanol) production process 100. As a general reference point, the dry grind method 100 can be divided into a front end and a back end. The part of the method 100 that occurs prior to distillation 110 is considered the "front end," and the part of the method 100 that occurs after distillation 110 is considered the "back end." To that end, the front end of the dry grind process 100 begins with a grinding step 102 in which dried whole corn kernels can be passed through hammer mills for grinding into meal or a fine powder. The screen openings in the hammer mills or similar devices typically are of a size 6/64 to 9/64 inch, or about 2.38 mm to 3.57 mm, but some plants can operate at less than or greater than these screen sizes. The resulting particle distribution yields a very wide spread, bell type curve, which includes particle sizes as small as 45 microns and as large as 2 mm to 3 mm. The majority of the particles are in the range of 500 to 1200 microns, which is the "peak" of the bell curve.

After the grinding step 102, the ground meal is mixed with cook water to create a slurry at slurry step 103 and a commercial enzyme called alpha-amylase is typically added (not shown). The slurry step 103 is followed by a liquefaction step 104 whereat the pH can be adjusted to about 4.8 to 5.8 and the temperature maintained between about 50° C. to 105° C. so as to convert the insoluble starch in the slurry to soluble starch. Various typical liquefaction processes, which occur at this liquefaction step 104, are discussed in more detail further below. The stream after the liquefaction step 104 has about 30% dry solids (DS) content, but can range from about 29-36%, with all the components contained in the corn kernels, including starch/sugars, protein, fiber, starch, germ, grit, oil, and salts, for example. Higher solids are achievable, but this requires extensive alpha amylase enzyme to rapidly breakdown the viscosity in the initial liquefaction step. There generally are several types of solids in the liquefaction stream: fiber, germ, and grit.

Liquefaction may be followed by separate saccharification and fermentation steps, 106 and 108, respectively, although in most commercial dry grind ethanol processes, saccharification and fermentation can occur simultaneously. This single step is referred to in the industry as "Simultaneous Saccharification and Fermentation" (SSF). Both saccharification and SSF can take as long as about 50 to 60 hours. Fermentation converts the sugar to alcohol. Yeast can optionally be recycled in a yeast recycling step (not shown) either during the fermentation process or at the very end of the fermentation process. Subsequent to the fermentation step 108 is the distillation (and dehydration) step 110, which utilizes a still to recover the alcohol.

Finally, a centrifugation step 112 involves centrifuging the residuals produced with the distillation and dehydration step 110, i.e., "whole stillage", in order to separate the insoluble solids ("wet cake") from the liquid ("thin stillage"). The liquid from the centrifuge contains about 5% to 12% DS. The "wet cake" includes fiber, of which there generally are three types: (1) pericarp, with average particle sizes typically about 1 mm to 3 mm; (2) tricap, with average particle sizes about 500 micron; (3) and fine fiber, with average particle sizes of about 250 microns. There may also be proteins with a particle size of about 45 microns to about 300 microns.

The thin stillage typically enters evaporators in an evaporation step 114 in order to boil or flash away moisture, leaving a thick syrup which contains the soluble (dissolved) solids (mainly protein and starches/sugars) from the fermentation (25 to 40% dry solids) along with residual oil and fine fiber. The concentrated slurry can be sent to a centrifuge to separate the oil from the syrup in an oil recovery step 116. The oil can be sold as a separate high value product. The oil yield is normally about 0.6 lb/bu of corn with high free fatty acids content. This oil yield recovers only about ⅓ of the oil in the corn, with part of the oil passing with the syrup stream and the remainder being lost with the fiber/wet cake stream. About one-half of the oil inside the corn kernel remains inside the germ after the distillation step 110, which cannot be separated in the typical dry grind process using centrifuges. The free fatty acids content, which is created when the oil is heated and exposed to oxygen throughout the front and back-end process, reduces the value of the oil. The (de-oil) centrifuge only removes less than 50% because the protein and oil make an emulsion, which cannot be satisfactorily separated.

The syrup, which may have more than 10% oil, can be mixed with the centrifuged wet cake, and the mixture may be sold to beef and dairy feedlots as Distillers Wet Grain with Solubles (DWGS). Alternatively, the wet cake and concentrated syrup mixture may be dried in a drying step 118 and sold as Distillers Dried Grain with Solubles (DDGS) to dairy and beef feedlots. This DDGS has all the corn and yeast protein and about 67% of the oil in the starting corn material. But the value of DDGS is low due to the high percentage of fiber, and in some cases the oil is a hindrance to animal digestion and lactating cow milk quality.

Figure 3:
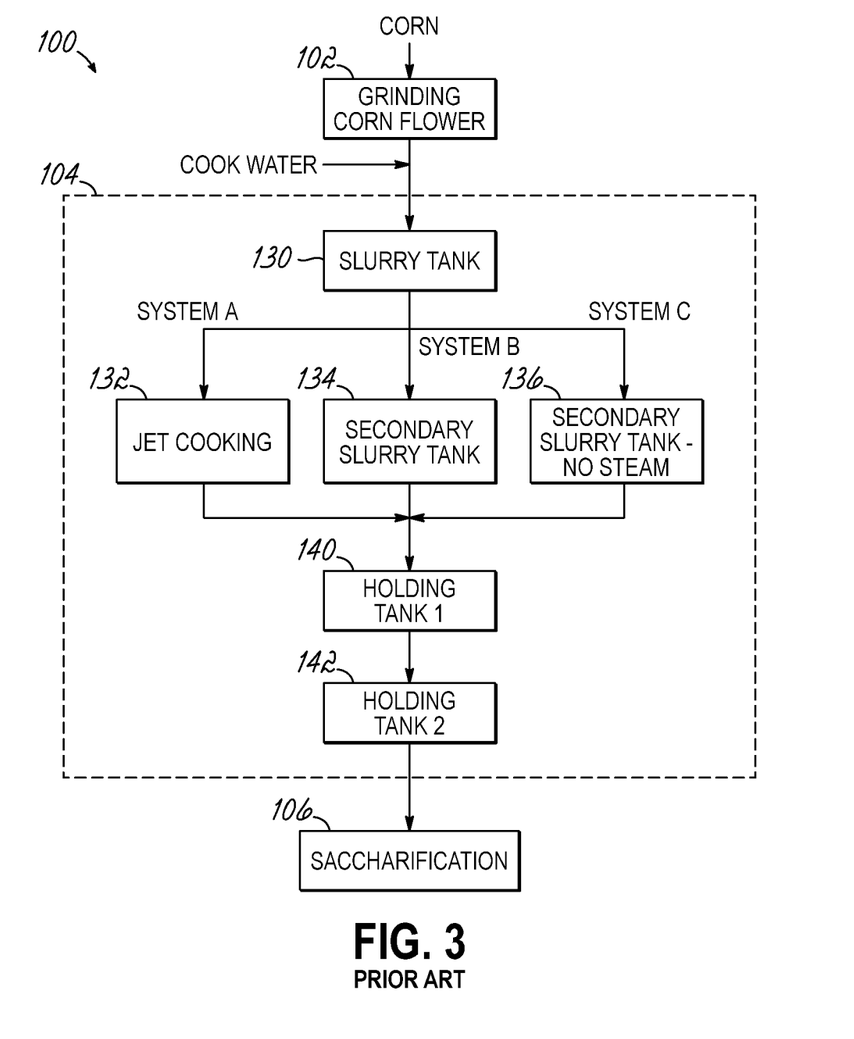
FIG. 3 is a flow diagram of various typical liquefaction processes in a typical dry grind alcohol production process.

Further, with respect to the liquefaction step 104, FIG. 3 is a flow diagram of various typical liquefaction processes that define the liquefaction step 104 in the dry grind process 100. Again, the dry grind process 100 begins with a grinding step 102 in which dried whole corn kernels are passed through hammer mills or similar milling systems such as roller mills, disc mill, flaking mills, impacted mill, or pin mills for grinding into meal or a fine powder. The grinding step 102 is followed by the liquefaction step 104, which itself includes multiple steps as is discussed next.

Each of the various liquefaction processes generally begins with the ground grain or similar material being mixed with cook and/or backset water, which can be sent from evaporation step 114 (FIG. 2), to create a slurry at slurry tank 130 whereat a commercial enzyme called alpha-amylase is typically added (not shown). The pH can be adjusted here, as is known in the art, to about 4.8 to 5.8 and the temperature maintained between about 50° C. to 105° C. so as to allow for the enzyme activity to begin converting the insoluble starch in the slurry to soluble liquid starch. Other pH ranges, such as from pH 3.5 to 7.0, may be utilized, and an acid treatment system using sulfuric acid, for example, can be used as well for pH control and conversion of the starches to sugars.

After the slurry tank 130, there are normally three optional pre-holding tank steps, identified in FIG. 3 as systems A, B, and C, which may be selected depending generally upon the desired temperature and holding time of the slurry. With system A, the slurry from the slurry tank 130 is subjected to a jet cooking step 132 whereat the slurry is fed to a jet cooker, heated to about 120° C., held in a U-tube or similar holding vessel for about 2 min to about 30 min, then forwarded to a flash tank. In the flash tank, the injected steam flashes out of the liquid stream, creating another particle size reduction and providing a means for recovering the injected stream. The jet cooker creates a sheering force that ruptures the starch granules to aid the enzyme in reacting with the starch inside the granule and allows for rapid hydration of the starch granules. It is noted here that system A may be replaced with a wet grind system. With system B, the slurry is subjected to a secondary slurry tank step 134 whereat the slurry is maintained at a temperature from about 90° C. to 100° C. for about 10 min to about 1 hour. With system C, the slurry from the slurry tank 130 is subjected to a secondary slurry tank—no steam step 136, whereat the slurry from the slurry tank 130 is sent to a secondary slurry tank, without any steam injection, and maintained at a temperature of about 80° C. to 90° C. for about 1 to 2 hours. Thereafter, the slurry from each of systems A, B, and C is forwarded, in series, to first and second holding tanks 140 and 142 for a total holding time of about 60 minutes to about 4 hours at temperatures of about 80° C. to 90° C. to complete the liquefaction step 104, which then is followed by the saccharification and fermentation steps 106 and 108, along with the remainder of the process 100 of FIG. 2. While two holding tanks are shown here, it should be understood that one holding tank, more than two holding tanks, or no holding tanks may be utilized.

In today's typical grain to biochemical plants (e.g., corn to alcohol plants), many systems, particularly dry grind systems, process the entire corn kernel through fermentation and distillation. Such designs require about 30% more front-end system capacity because there is only about 70% starch in corn, with less for other grains and/or biomass materials. Additionally, extensive capital and operational costs are necessary to process the remaining non-fermentable components within the process. By removing undesirable, unfermentable components prior to fermentation (or other reaction process), more biochemical, biofuel, and other processes become economically desirable.

It thus would be beneficial to provide an improved dry milling system and method that produces a sugar stream, such as for biochemical production, that may be similar to the sugar stream produced by conventional wet corn milling systems, but at a fraction of the cost and generate additional revenue from high value by-products, such as oil, protein, and/or fiber, for example, with desirable yield.

SUMMARY OF THE INVENTION

The present invention provides for a dry milling system and method that produces a sugar stream, such as for biochemical production, that may be similar to the sugar stream produced by conventional wet corn milling systems, but at a fraction of the cost, and generate additional revenue from high value by-products, such as oil, protein and/or fiber, for example, with desirable yield.

In one embodiment, a method for producing a sugar stream is provided and includes mixing ground grain particles with a liquid to provide a slurry, then separating the slurry into an initial solids portion and an initial liquid portion. The method further includes subjecting the initial solids portion to liquefaction to provide a first liquefied starch solution including starch and subjecting at least a portion of the initial liquid portion to a separate liquefaction step to provide a second liquefied starch solution including starch. Thereafter, the second liquefied starch solution is subjected to saccharification to convert the starch to simple sugars and produce a saccharified stream including the simple sugars. And after saccharification of the initial liquid portion but prior to further processing of the simple sugars, the saccharified stream is separated into a solids portion and a liquid portion including the simple sugars, wherein the separated liquid portion from the saccharified stream defines a sugar stream having a dextrose equivalent of at least 20 DE and a total unfermentable solids fraction that is less than or equal to 30% of a total solids content. In one example, the method can further include subjecting the first liquefied starch solution to a separate saccharification step from the initial liquid portion to convert the starch in the first liquefied starch solution to simple sugars and produce a saccharified stream including the simple sugars for further processing.

In another embodiment, a system for producing a sugar stream is provided that includes a slurry tank in which ground grain particles mix with a liquid to provide a slurry. A solid/liquid separation device is situated after the slurry tank and receives the slurry and separates the slurry into an initial solids portion and an initial liquid portion. A first liquefaction system is situated after the solid/liquid separation device and receives the initial solids portion to provide a first liquefied starch solution including starch. A second liquefaction system is situated after the solid/liquid separation device and receives the initial liquid portion to provide a second liquefied starch solution including starch. A first saccharification system is situated after the first liquefaction system and receives the first liquefied starch solution to convert the starch to simple sugars and produce a first saccharified stream including the simple sugars. A second saccharification system is situated after the second liquefaction system and receives the second liquefied starch solution to convert the starch to simple sugars and produce a second saccharified stream including the simple sugars. A sugar separation device is situated after the second saccharification system and receives and separates the second saccharified stream into a solids portion and a liquid portion including the simple sugars, wherein the separated liquid portion from the second saccharified stream defines a sugar stream having a dextrose equivalent of at least 20 DE and a total unfermentable solids fraction that is less than or equal to 30% of a total solids content.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

FIGS. 1 and 2 have been discussed above and represent flow diagrams of a typical wet mill and dry grind alcohol production process, respectively. FIG. 3, likewise, has been discussed above and represents various typical liquefaction processes in a typical dry grind alcohol production process.

Figure 4:
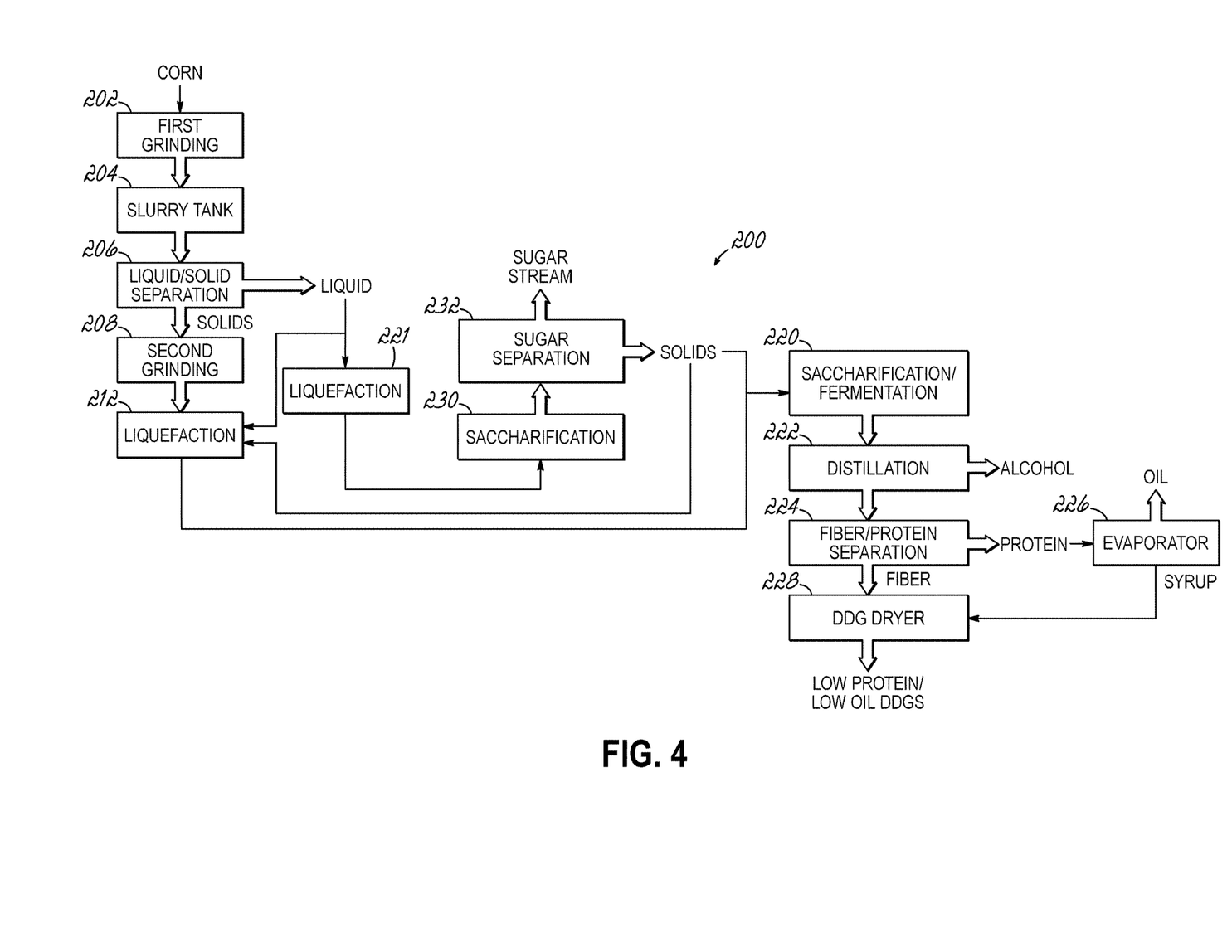
FIG. 4 is a flow diagram showing a dry grind system and method for producing a sugar stream in accordance with an embodiment of the invention.

FIG. 4 illustrates an embodiment of a dry grind system and method 200 for producing a sugar stream from grains or similar carbohydrate sources and/or residues, such as for biochemical production, in accordance with the present invention. As further discussed in detail below, a sugar/carbohydrate stream, which includes a desired Dextrose Equivalent (DE) where DE describes the degree of conversion of starch to dextrose (a.k.a. glucose) and/or has had removed therefrom an undesirable amount of unfermentable components can be produced after saccharification and prior to fermentation (or other sugar utilization/conversion process), with such sugar stream being available for biochemical production, e.g., alcohol production, or other processes. In other words, sugar stream production and grain component separation occurs on the front end of the system and method 200.

For purposes herein, in one example, the resulting sugar stream that may be desirable after saccharification, but before fermentation, such as for use in biochemical production, can be a stream where the starch/sugars in that stream define at least a 90 DE and/or where the total insoluble (unfermentable) solids fraction of the stream is less than or equal to 7% of the total solids content in the stream. In other words, at least 90% of the total starch/sugar in that stream is dextrose and/or no greater than 7% of the total solids in that stream includes non-fermentable components. In another example, the sugar stream may define at least 95 DE. In another example, the resulting sugar stream may define at least 98 DE. In yet another example, the starch/sugars in the stream can define at least a 20, 30, 40, 50, 60, 70, or 80 DE. In another example, the total insoluble (unfermentable) solids fraction of the stream is less than or equal to 3% of the total solids content in the stream. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%. In other words, the total fermentable content (fermentable solids fraction) of the stream may be no more than 30%, 40%, 50%, 60%, 70%, 75%, 80%, 85%, 90%, 95%, 97%, or 99% of the total solids content in the stream. In another example, on a dry mass basis, the weight % fermentable material in the sugar stream that may be desired is greater than or equal to 80%. In another example, on a dry mass basis, the weight % fermentable material in a sugar stream is greater than or equal to 85%, 90%, 95%, 98%, or 99%.

In addition, although the system and method 200 described herein will generally focus on corn or kernel components, virtually any type of grain, whether whole and fractionated or any carbohydrate source, including, but not limited to, wheat, barley, sorghum, rye, rice, oats, sugar cane, tapioca, cassava, pea, or the like, as well as other biomass products, can be used. And broadly speaking, it should be understood that the entire grain or biomass or less than the entire grain, e.g., corn and/or grit and/or endosperm or biomass, may be ground and/or used in the system and method 200.

With further reference now to FIG. 4, in this dry grind system and method 200, grains such as corn and/or corn particles, for example, can be subjected to an optional first grinding step 202, which involves use of a hammer mill, roller mill, pin mill, impact mill, flaking mill, or the like, either in series or parallel, to grind the corn and/or corn particles to particle sizes less than about 7/64 inch or, in another example, less than about 10/64 inch and allow for the release of oil therefrom to define free oil. In one example, the screen size for separating the particles can range from about 24/64 inch to about 2/64 inch. In another example, the resulting particle sizes are from about 50 microns to about 3 mm. The grinding also helps break up the bonds between the fiber, protein, starch, and germ. In one example, screen size or resulting particle size may have little to no impact on the ability to separate the sugar from the remaining kernel or similar raw material component(s). If the carbohydrate source is pre-ground or initially in particulate form, the optional grind step 202 may be excluded from the system and method 200.

Next, the ground corn flour can be mixed with backset liquid at slurry tank 204 to create a slurry. Optionally, fresh water may be added so as to limit the amount of backset needed here. An enzyme(s), such as alpha amylase, optionally can be added to the slurry tank 204 or in a slurry blender (not shown) between the first grinding step 202 and the slurry tank 204. The slurry may be heated at the slurry tank 204 from about 66° C. (150° F.) to about 93° C. (200° F.) for about 10 min to about 120 min. The stream from the slurry tank 204 contains about 0.5 lb/bu free oil, about 1.5 lb/bu germ (particle size ranges from about 50 microns to about 3 mm), about 1.8 lb/bu grit (particle size ranges from about 50 microns to about 3 mm), which can include starch, and about 4.25 lb/bu fiber (particle size ranges from about 50 microns to about 3 mm).

The stream from the slurry tank 204 next may be subjected to a liquid/solid separation step 206 to remove a desired amount of liquids therefrom. The liquid/solid separation step 206 can separate a generally liquefied solution (about 60% to about 80% by volume), which includes free oil, protein, and fine solids (which do not need grinding), from heavy solids cake (about 20% to about 40% by volume), which includes the heavier fiber, grit, and germ, which can include bound oil, protein, and/or starch. That is, the liquid/solid separation step 206 can separate out at least a portion of the liquefied solution from the heavy solids cake to define an initial liquid portion. In one example, at least a majority or all of the liquefied solution can be separated from the heavy solids cake to provide the initial liquid portion. The liquid/solid separation step 206 uses dewatering equipment, e.g., a paddle screen, a vibration screen, screen decanter centrifuge or conic screen centrifuge, a pressure screen, a preconcentrator, a filter press, or the like, to accomplish separation of the solids from the liquid portion. The fine solids can be no greater than 200 microns. In another example, the fine solids are no greater than 500 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about ⅙ to about ½ of the screen diameter. The number of paddles on the paddle screen and the conveyor pitch on the preconcentrator can be modified depending on the amount of solids in the feed. The gap between the paddle screen and paddle can range from about 0.04 to about 0.2 inch. A smaller gap gives a drier cake with higher capacity and purer fiber but loses more fiber to filtrate. A larger gap gives a wetter cake with lower capacity and purer liquid (less insoluble solid). The paddle speed can range from 400 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 45 microns to about 500 microns. In another example, the screen openings can range from 100 to 300 microns. In yet another example, the screen openings can range from 200 to 250 microns. Smaller screen openings tend to increase the protein/oil/alcohol yield with higher equipment and operation cost, whereas larger screen openings tend to lower protein/oil/alcohol yield with less equipment and operation cost.

The wet cake or dewatered initial solids portion at the liquid/solid separation step 206 (about 60% to about 65% water), along with any remaining portion of the liquefied solution, next may be subjected to an optional second grinding/particle size reduction step 208, which may involve use of a disc mill, hammer mill, a pin or impact mill, a roller mill, a grind mill, or the like, to further grind the corn particles to particle sizes less than about 850 microns and allow for additional release of oil and protein/starch complexes therefrom. In another example, the particle sizes are from about 300 microns to about 650 mm. The grinding further helps continue to break up the bonds between the fiber, protein, and starch and facilitates the release of free oil from germ particles. The stream from the second grinding/particle size reduction step 208 contains about 0.1 lb/bu to about 1.0 lb/bu free oil. After milling, the milled solids, along with any portion of liquefied solution, can be sent on and subjected to a liquefaction step 212, such solids optionally may be mixed with solids from filtration/membrane separation step 232, as described further below.

The liquefaction step 212 can include multiple steps as discussed above and shown in FIG. 3. In one embodiment, the pH can be adjusted here to about 5.2 to about 5.8 and the temperature maintained between about 50° C. to about 105° C. so as to convert the insoluble starch in the stream to soluble or liquid starch. Other pH ranges, such as from pH 3.5-7.0, may be utilized and an acid treatment system using sulfuric acid, for example, may be used as well for pH control and for conversion of the starches to sugars. The stream may be further subjected to jet cooking whereat the slurry is fed to a jet cooker, heated to about 120° C., held for about 2 min to about 30 min, then forwarded to a flash tank. The jet cooker creates a sheering force that ruptures the starch granules to aid the enzyme in reacting with the starch inside the granule and for hydrating the starch molecules. In another embodiment, the stream can be subjected to a secondary slurry tank whereat steam is injected directly to the secondary slurry tank and the slurry is maintained at a temperature from about 80° C. to about 100° C. for about 30 min to about one hour. In yet another embodiment, the stream can be subjected to a secondary slurry tank with no steam. In particular, the stream is sent to a secondary slurry tank without any steam injection and maintained at a temperature of about 80° C. to about 90° C. for 1 to 2 hours. Thereafter, the liquefied slurry may be forwarded to a holding tank for a total holding time of about 1 hour to about 4 hours at temperatures of about 80° C. to about 90° C. to complete the liquefaction step 212. With respect to the liquefaction step 212, pH, temperature, and/or holding time may be adjusted as desired.

The stream after the liquefaction step 212 can have about 28% to about 40% dry solids (DS) content with most of the components contained in the corn kernels, including starches/sugars, protein, fiber, germ, grit, oil, and salts, for example. There generally are three types of solids in the liquefaction stream: fiber, germ, and grit, which can include starch and protein, with all three solids having about the same particle size distribution. The stream from the liquefaction step 212 can contain about 1 lb/bu free oil, about 1.5 lb/bu germ particle (size ranges from less about 50 microns to about 1 mm), about 4.5 lb/bu protein (size ranges from about 50 microns to about 1 mm), and about 4.25 lb/bu fiber (particle size ranges from about 50 microns to about 3 mm). The stream from the liquefaction step 212 can be sent to the saccharification/fermentation step 220 and processed as further discussed below.

Returning now to the separated liquid portion or liquefied starch solution of the liquid/solid separation step 206, the initial liquid portion can be sent on and subjected to an optional second liquefaction step 221. In one example, a portion of the initial liquid portion can be sent to and subjected to liquefaction step 212 instead of being subjected to second liquefaction step 221. Like liquefaction step 212, second liquefaction step 221 can include multiple steps as discussed above and shown in FIG. 3.

The stream from the second liquefaction step 221 can be sent to an optional saccharification step 230 whereat the starches, including complex carbohydrate and oligosaccharides, can be further broken down into simple sugar molecules (i.e., dextrose) to produce a saccharified mash. In particular, at the saccharification step 230, the stream may be subjected to a two-step conversion process. The first part of the cook process, in one example, includes adjusting the pH to about 3.5 to about 7.0, with the temperature being maintained between about 30° C. to about 100° C. for 1 to 6 hours to further convert the insoluble starch in the slurry to soluble starch, particularly dextrose. In another example, the pH can be adjusted to about 4.8 to 5.8 or 5.5, for example. In another example, the temperature can be maintained at 80° C. for about 5 hours. Also, an enzyme, such as alpha-amylase, may be additionally added here. In one example, the amount of alpha-amylase may be from about 0.0035 wt % to about 0.04 wt % of the slurry stream. In another example, the amount of alpha-amylase may be from about 0.02 wt % to about 0.1 wt % of the total stream.

The second part of the cook process, in one example, may include adjusting the pH to about 3.5 to 5.0, with the temperature being maintained between about 30° C. to about 100° C. for about 10 minutes to about 5 hours so as to further convert the insoluble starch in the slurry to soluble starch, particularly dextrose. In another example, the pH can be 4.5. In another example, the temperature can be maintained from about 54° C. (130° F.) to about 74° C. (165° F.) for about 4 hours or up to about 60 hours. An enzyme, such as glucoamylase, also may be added here. In one example, the amount of glucoamylase may be from about 0.01 wt % to about 0.2 wt % of the stream. In another example, the amount of glucoamylase may be from about 0.08 to about 0.14 wt % of the stream. Other enzymes or similar catalytic conversion agents may be added at this step or previous steps that can enhance starch conversion to sugar or yield other benefits, such as fiber or cellulosic sugar release, conversion of proteins to soluble proteins, or the release of oil from germ.

A saccharified sugar stream having a density of about 1.05 grams/cc to about 1.15 grams/cc can result here. At this point, the saccharified sugar stream may be no less than about 90 DE. In another example, the saccharified sugar stream may be no less than 20, 30, 40, 50, 60, 70, or 80 DE. In this example, the saccharified sugar stream may not be considered desirable or "clean" enough, such as for use in biochemical (e.g., biofuel) production, because the total fermentable content of the stream may be no more than 75% of the total solids content in the stream. In this example, the saccharified sugar stream can have a total solids fraction of about 22% to about 40%, such solids including sugar, starch, fiber, protein, germ, oil, and ash, for example. In yet another example, the total fermentable content of the stream is no more than 30, 40, 50, 60, 70% or 80% of the total solids content in the stream. The remaining solids are fiber, protein, oil, and ash, for example. The stream from the saccharification step 230 contains about 0.1 lb/bu to about 1.0 lb/bu free oil.

After the saccharification step 230 (but before any potential fermentation or processing of the sugar stream), so as to provide a more desirable sugar stream, the saccharified sugar stream can be subjected to a sugar separation step 232, which can include a cyclone, decanter, disc centrifuge, rotary vacuum filter, microfilter/microfiltration, membrane filtration, ultrafiltration, precoat/diatomaceous earth filter, or the like, to produce a more desirable sugar stream, which may be considered a purified or refined sugar stream, by further separating out any remaining insoluble components, color, ash, minerals, or the like. In one example, the filter screen size here may be from about 0.1 micron to about 100 microns. In another example, the filter screen size may be from about 5 microns to about 50 microns. Due to the input of water, the sugar stream can have a total solids fraction of 20-35%. In this example, the sugar stream here may be considered purified or refined enough because the total insoluble (unfermentable) solids fraction of the stream is less than 10%. In another example, the total insoluble (unfermentable) solids fraction of the stream is less than or equal to 5%. In another example, the total insoluble (unfermentable) solids fraction of the stream is less than or equal to 3%. In another example, the total insoluble (unfermentable) solids fraction of the stream is less than or equal to 1%. In still another example, the total insoluble (unfermentable) solids fraction of the stream is less than or equal to 10%, 15%, 20%, 25%, or 30%.

The sugar separation step 232 may be replaced by, or additionally include, a cyclone, a decanter, a disc centrifuge, ultrafiltration, carbon column color removal, filter press, flotation, adsorption, and/or demineralization technologies (e.g., ion exchange), either in series or parallel. Resin refining, which includes a combination of carbon filtration and demineralization in one step, can also be utilized for refining the sugars. Additionally, due to a low solids content of the sugar stream here, an optional evaporation step (not shown) may be added hereafter to further concentrate the total solids fraction.

The sugar stream from the sugar separation step 232 can be sent on to a further processing step, such as a fermentation step where the sugars are converted, e.g., via a fermenter, to alcohol, such as ethanol or butanol or any other fermentation conversion process or similar sugar utilization/conversion process, followed by distillation and/or separation of the desired component(s) (not shown), which can recover the alcohol or byproduct(s)/compound(s) produced, as is known in the art. The sugar stream can allow for recovery of a fermentation agent from the fermentation step. The fermentation agent can be recovered by means known in the art and can be dried as a separate product or, for example, can be sent to a protein separation step or other streams/steps, in the system and method 200, which can allow for capture of the fermentation agent and/or used for further processing. Fermentation agent (such as yeast or bacteria) recycling can occur by use of a clean sugar source. Following distillation or desired separation step(s), the system and method 200 can include any back end type process(es), which may be known or unknown in the art to process, for example, the whole stillage. The fermentation step may be part of an alcohol production system that receives a sugar stream that is not as desirable or clean, i.e., "dirtier," than the sugar stream being sent and subjected to the same fermentation step as the dirty sugar stream. Other options for the sugar stream, aside from fermentation, can include further processing or refining of the glucose to fructose or other simple or even complex carbohydrates, processing into feed, microbe-based fermentation (as opposed to yeast based) and other various chemical, pharmaceutical or nutraceutical processing (such as propanol, isobutanol, citric acid or succinic acid), and the like. Such processing can occur via a reactor, including, for example, a catalytic or chemical reactor. In one example, the reactor is a fermenter.

Still referring to FIG. 4, at least a portion of the solid or heavy components (raffinate) from the sugar separation step 232 may be sent to the liquefaction step 212, and combined and processed with the stream from the second grinding step 208, as discussed above, and/or can be combined together with the stream from the liquefaction step 212 and sent to saccharification/fermentation step 220. These heavier components or underflow from the sugar separation step 232, can be more concentrated in total solids, at about 28% with a potential range of 25-40%.

Concerning now the saccharification/fermentation step 220, although illustrated in a single box and as would be understood, saccharification and fermentation may occur separately here, in order, or may occur simultaneously. Both processes, i.e., saccharification and fermentation, are described in detail above. Generally, the stream from the liquefaction step 212, alone or combined with the solids from the sugar separation step 232, can be subjected to saccharification whereat complex carbohydrate and oligosaccharides can be further broken down into simple molecules (i.e., dextrose) to produce a saccharified mash. With fermentation, the glucose sugars are metabolized into ethanol and $CO_2$. Other options for the solids stream, aside from fermentation in the saccharification/fermentation step 220, can include further processing or refining of the solids into feed, microbe based fermentation (as opposed to yeast based) and other various chemical, pharmaceutical or nutraceutical processing (such as propanol, isobutanol, citric acid or succinic acid), and the like. Such processing can occur via a reactor, which can include a fermenter.

The saccharification/fermentation step 220 is followed by distillation 222. At the distillation tower, the fermented solution is separated from the stillage, which includes fiber, protein, and germ particles, to produce alcohol. The fiber can be separated from the germ particles and protein (gluten) at a fiber/protein separation step 224 by differences in particle sizes using a screen device, such as a filtration centrifuge, a filtration decanter, a paddle screen, a pressure screen, or the like to remove the fiber therefrom. The screen openings normally will be about 500 microns to capture amounts of tipcap, pericarp, as well as fine fiber, but can range from about 200 microns to about 2,000 microns. The separated fiber is used to produce a low protein (less than about 25%)/low oil (less than about 8%) DDG.

If a lower protein and oil content in the fiber is needed or desired, the fiber may be sent to a holding tank (not shown), for example, whereat the pH of the separated fiber can be adjusted to about 7.5 to about 10.5 (or about 8 to about 9.5), such as by the addition of chemicals, e.g., sodium hydroxide, lime, sodium carbonate, trisodium phosphate, or the like to help release additional oil from the germ. Also, cell wall breaking enzymes, e.g., protease, cellulase, hemicellulose, phytase, and the like, and/or chemicals, e.g., sodium sulfite and the like, may be added here to help release additional oil from the germ. In one example, the fiber can be held in the tank for about 1 hour at a temperature of about 140° F. to about 200° F. (or about 180° F. to about 200° F.). Thereafter, the fiber can be subjected to a grind step to release more oil and protein from the fiber. The fiber produced by these additional treatment steps can give a much lower oil (less than 2%) and lower protein (less than 10%) and can be used for secondary alcohol production.

The centrate from the fiber/protein separation step 224 goes to an evaporator 226 to separate any oil therefrom and to produce syrup, which can be mixed with the DDG and dried, as represented by numeral 228, to give the low protein (less than about 25%)/low oil (less than about 8%) DDGS, such as for cows or pigs, particularly dairy cows. The DDGS contains less than about 25% protein, less than about 8% oil, and less than about 5% starch.

In addition, an optional centrifugation step (not shown) may be provided to recover the xanthophyll content in the emulsion layer of the recovered oils, both prior to and after saccharification in the saccharification/fermentation step 220, and mixed with the protein by-product prior to drying to increase the feed value. The overflow from the centrifuge(s) can go back to the oil storage tanks (not shown).

Also, further modifications can be made to the above system and method 200 to improve co-product recovery, such as oil recovery using surfactants and other emulsion-disrupting agents. In one example, emulsion-disrupting agents, such as surfactants, or flocculants may be added prior to steps in which emulsions are expected to form or after an emulsion forms in the method. For example, emulsions can form during centrifugation such that incorporation of surfactants prior to or during centrifugation can improve oil separation and recovery. In one example, the syrup stream pre-oil separation can also have emulsion breakers, surfactants, and/or flocculants added to the evaporation system to aid in enhancing the oil yield. This may result in an additional 0.05 to 0.5 lb/bu oil yield gain.

While the present invention has been illustrated by a description of various embodiments and while these embodiments have been described in considerable detail, it is not the intention of the applicant to restrict or in any way limit the scope of the appended claims to such detail. For example, various enzymes (and types thereof) such as amylase, alpha-amylase, glucoamylase, fungal, cellulase, hemicellulase, protease, phytase, and the like can be optionally added, for example, before, during, and/or after any number of steps in the system and method 200 including the slurry tank 204 the second grinding step 208 the liquefaction step 212 and/or the saccharification step 230 such as to enhance the separation of components, such as to help break the bonds between protein, starch, and fiber and/or to help convert starches to sugars and/or help to release free oil. In addition, temperature, pH, surfactant, and/or flocculant adjustments may be adjusted, as needed or desired, at the various steps throughout the system and method 200 including at the slurry tank 204, etc., such as to optimize the use of enzymes or chemistries. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A method for producing a sugar stream comprising:
   mixing ground grain particles with a liquid to provide a slurry;
   separating the slurry into an initial solids portion and an initial liquid portion,
   subjecting the initial solids portion to liquefaction to provide a first liquefied starch solution including starch and the initial solids and subjecting at least a portion of the initial liquid portion to a separate liquefaction step to provide a second liquefied starch solution including starch;
   thereafter, subjecting the second liquefied starch solution to saccharification to convert the starch to simple sugars and produce a saccharified stream including the simple sugars; and
   after saccharification of the second liquefied starch solution but prior to further processing of the simple sugars, separating the saccharified stream into a solids portion and a liquid portion including the simple sugars,
   wherein, prior to separating the saccharified stream into the solids portion and the liquid portion, the separated initial solids remain separate from the saccharified stream of the second liquefied starch solution and wherein the separated liquid portion from the saccharified stream defines a sugar stream having a dextrose equivalent of at least 20 DE and a total unfermentable solids fraction that is less than or equal to 30% of a total solids content.

2. The method of claim 1 further comprising subjecting the first liquefied starch solution to a separate saccharification step from the initial liquid portion to convert the starch in the first liquefied starch solution to simple sugars and produce a saccharified stream including the initial solids and the simple sugars for further processing, wherein, prior to separation of the saccharified stream of the second liquefied starch solution into the solids portion and the liquid portion including the simple sugar, the saccharified stream of the second liquefied starch solution remains separate from the saccharified stream of the first liquefied starch solution.

3. The method of claim 2 further comprising subjecting at least a portion of the separated solids portion from the saccharified stream to the separate saccharification step along with the first liquefied starch solution.

4. The method of claim 2 further comprising subjecting at least a portion of the separated solids portion from the saccharified stream to liquefaction along with the initial solids portion and subjecting at least a portion of the separated solids portion from the saccharified stream to the separate saccharification step along with the first liquefied starch solution.

5. The method of claim 2 wherein the further processing of the saccharified stream including the simple sugars from the separate saccharification step comprises fermentation followed by distillation to produce an alcohol.

6. The method of claim 5 wherein fermentation and the separate saccharification step occur simultaneously.

7. The method of claim 1 further comprising, after separating the slurry into an initial solids portion and an initial liquid portion and prior to subjecting the initial solids portion to liquefaction, subjecting the initial solids portion to grinding.

8. The method of claim 1 further comprising subjecting at least a portion of the separated solids portion from the saccharified stream to liquefaction along with the initial solids portion.

9. The method of claim 1 wherein separating the saccharified stream into a solids portion and a liquid portion including the simple sugars comprises, after saccharification of the second liquefied starch solution but prior to further processing of the simple sugars, separating, via a membrane or filtration device, the saccharified stream into the solids portion and the liquid portion.

10. The method of claim 1 further comprising subjecting the sugar stream to a sugar conversion process to produce a biochemical.

11. The method of claim 10 wherein the sugar conversion process is fermentation.

12. The method of claim 10 wherein the sugar conversion process includes a catalytic or chemical reaction.

13. The method of claim 10 further comprising subjecting the first liquefied starch solution to a separate saccharification step from the initial liquid portion to convert the starch in the first liquefied starch solution to simple sugars and produce a saccharified stream including the initial solids and the simple sugars, and subjecting the simple sugars of the saccharified stream of the first liquefied starch solution to a sugar conversion process that is separate from the sugar conversion process of the sugar stream.

14. The method of claim 13 wherein the sugar conversion processes are separate fermentation processes.

15. The method of claim 1 further comprising grinding grain and/or grain components into the ground grain particles.

16. The method of claim 1 wherein the initial liquid portion includes at least a majority of the liquid from the slurry.

17. The method of claim 1 further comprising subjecting at least a portion of the initial liquid portion, along with the initial solids portion, to liquefaction to provide the first liquefied starch solution.

18. A method for producing a sugar stream comprising:
   mixing ground grain particles with a liquid to provide a slurry;
   separating the slurry into an initial solids portion and an initial liquid portion,
   subjecting the initial solids portion to liquefaction to provide a first liquefied starch solution including starch and subjecting at least a portion of the initial liquid portion to a separate liquefaction step to provide a second liquefied starch solution including starch;
   thereafter, subjecting the second liquefied starch solution to saccharification to convert the starch to simple sugars and produce a saccharified stream including the simple sugars; and
   after saccharification of the second liquefied starch solution but prior to further processing of the simple sugars, separating the saccharified stream into a solids portion and a liquid portion including the simple sugars,
   wherein the separated liquid portion from the saccharified stream defines a sugar stream having a dextrose equivalent of at least 20 DE and a total unfermentable solids fraction that is less than or equal to 30% of a total solids content, and wherein at least a portion of the separated solids portion from the saccharified stream is subjected to liquefaction along with the initial solids portion.

19. The method of claim 18 further comprising subjecting at least a portion of the separated solids portion from the saccharified stream to a separate saccharification step along with the first liquefied starch solution to produce a separate saccharified stream including the simple sugars.

20. The method of 19 further comprising subjecting the separate saccharified stream including the simple sugars to fermentation followed by distillation to produce an alcohol.

21. The method of claim 20 wherein fermentation and the separate saccharification step occur simultaneously.

22. The method of claim 18 further comprising, after separating the slurry into an initial solids portion and an initial liquid portion and prior to subjecting the initial solids portion to liquefaction, subjecting the initial solids portion to grinding.

23. The method of claim 18 wherein separating the saccharified stream into a solids portion and a liquid portion including the simple sugars comprises, after saccharification of the second liquefied starch solution but prior to further processing of the simple sugars, separating, via a membrane or filtration device, the saccharified stream into the solids portion and the liquid portion.

24. The method of claim 18 further comprising subjecting the sugar stream to a sugar conversion process to produce a biochemical.

25. The method of claim 24 wherein the sugar conversion process is fermentation.

26. The method of claim 24 wherein the sugar conversion process includes a catalytic or chemical reaction.

27. The method of claim 18 further comprising grinding grain and/or grain components into the ground grain particles.

* * * * *